United States Patent
Chiu et al.

(10) Patent No.: US 6,579,096 B2
(45) Date of Patent: Jun. 17, 2003

(54) METHOD AND SYSTEM FOR SELECTIVELY STAINING DENTAL COMPOSITE RESIN

(75) Inventors: Paul C. Chiu, 128 Ada Ave., #7, Mountain View, CA (US) 94043; Catherine Hoffmann, San Jose, CA (US)

(73) Assignee: Paul C. Chiu, Los Altos, CA (US)

( * ) Notice: Subject to any disclaimer, the term of this patent is extended or adjusted under 35 U.S.C. 154(b) by 0 days.

(21) Appl. No.: 09/924,405

(22) Filed: Aug. 7, 2001

(65) Prior Publication Data

US 2002/0068259 A1 Jun. 6, 2002

Related U.S. Application Data

(60) Provisional application No. 60/223,854, filed on Aug. 8, 2000.

(51) Int. Cl.[7] .............................. A61C 5/00; A61C 5/04
(52) U.S. Cl. ...................................... 433/215; 433/226
(58) Field of Search ................................ 433/215, 226, 433/228.1

(56) References Cited

U.S. PATENT DOCUMENTS

| | | | | | |
|---|---|---|---|---|---|
| 3,018,778 | A | * | 1/1962 | Brilliant | 433/226 |
| 3,902,969 | A | * | 9/1975 | Gold | 433/36 |
| 3,965,577 | A | * | 6/1976 | Wegner | 433/215 |
| 4,459,277 | A | * | 7/1984 | Kosti | 424/7.1 |
| 4,744,759 | A | * | 5/1988 | Bowen | 433/228.1 |
| 5,211,748 | A | * | 5/1993 | Robinson et al. | 433/228.1 |
| 5,719,031 | A | * | 2/1998 | Haugland et al. | 435/7.4 |
| 5,954,996 | A | * | 9/1999 | Discko, Jr. | 252/79.1 |

* cited by examiner

*Primary Examiner*—John J. Wilson
(74) *Attorney, Agent, or Firm*—Townsend and Townsend and Crew LLP

(57) ABSTRACT

A method and system for selectively staining dental composite materials includes an applicator (104) and a disclosing agent (102). In one embodiment, the applicator (104) provides the disclosing agent (102) to a tooth surface and a composite filling of the tooth. The composite filling is selectively stained to reveal the presence and location of the composite filling. In another embodiment, the tooth surface is selectively stained to reveal the presence and location of the composite filling.

25 Claims, 8 Drawing Sheets

METHOD AND SYSTEM FOR SELECTIVELY STAINING DENTAL COMPOSITE RESIN

CROSS REFERENCE TO RELATED APPLICATIONS

The present application claims benefit of U.S. Provisional Application Ser. No. 60/223,854, filed Aug. 8, 2000, the complete disclosure of which is incorporated herein by reference.

FIELD OF THE INVENTION

The present invention relates to dental techniques and, more particularly, to restorative techniques for composite resin materials.

BACKGROUND

Fillings have long been and likely will continue to be used in restorative dentistry to treat cavities in teeth. After excessive wear, marginal leakage, recurrent caries, a filling may damage, requiring either repair or replacement. However, prior art techniques proposed to repair and replace fillings have been disadvantageous in many respects. To date, the conventional repair or replacement of fillings, especially composite fillings, entail various difficulties.

The loss of tooth structure resulting from dental caries, or tooth decay, is commonly known as a cavity. The formation of a cavity is an invasive process affecting the structure of a tooth. A tooth has several layers. In basic terms, the outermost layer, the enamel, is the hardest and most mineralized substance in the body. Below the gum-line, a substance called cementum covers the tooth roots. Under both the enamel and the cementum is the dentin. The dentin, which is almost as hard as bone, contains nerve endings. Below the dentin is the dental pulp. The dental pulp is a vascular tissue, including capillaries, blood vessels, connective tissue, nerve fibers, and cells, which include odontoblasts, fibroblasts, macrophages, and lymphocytes. The dental pulp nourishes the tooth during development of the tooth.

A cavity is an infection caused by the interaction of dietary carbohydrates and bacteria found in the mouth. Proteins in saliva and food debris are combined with the bacteria to form a film known as plaque. The plaque coats the tooth with the bacteria. The most common forms of bacteria believed to play a role in the formation of cavities include *Streptococcus mutans, Lactobacillus casei* and *acidophilus,* and *Actinomyces naeslundi.*

These bacteria consume the carbohydrates of food debris, resulting in acid production. Exposure of the tooth to such acid decreases the PH at the tooth surface. The acid dissolves the enamel, initiating the formation of the cavity. As the cavity progresses, it invades the softer dentin directly beneath the enamel. Ultimately, the cavity may encroach on the nerve and blood supply of the tooth contained in the dental pulp.

The formation of a cavity occurs in two primary ways. First, cavities may form through pits and fissures. Pits and fissures are relatively thin areas of enamel that contain recesses that can trap food and plaque, thus allowing the production of acid. The cavities can typically attack a small, focused area at a vulnerable region and then spread widely to invade the underlying dentin. Second, cavities can attack a relatively smooth surface of the tooth, such as the front or back of a tooth, or in between teeth. Over the smooth surface, the thickness of the enamel is usually more uniform, and not reduced as in the case for pits and fissures. The production of acid can create a cavity with a wide area of attack, which converges as it penetrates deeper layers of the tooth.

Once discovered, the decayed, or carious, tooth structure must be removed before the typical placement of a filling in the cavity. Various removal techniques have been proposed and employed. For example, dental caries or decayed tooth structure has traditionally been removed by a dentist using a dental handpiece and a bur (the dental drill). More recent advances in dental technology and equipment presently also allow removal of decayed tooth structure by laser and air abrasion (micro sandblasting). Hand instruments may also be used in conjunction with one of the above methods. The procedure of caries removal first involves identification of the affected portion of the tooth. This may involve visual detection, tactile detection (e.g. with a dental explorer instrument), a dental x-ray, or a combination of the above. After identification, the area of decay may be removed by use of a dental handpiece and the decay is "drilled" out.

Typically it is desirable that only the area of actual decay is removed. Surrounding healthy or undecayed tooth structure would ideally be preserved and not be removed. During the active procedure of caries removal, the continued presence of decayed tooth is usually determined by the visual appearance and/or surface hardness of the affected area as decayed areas are usually stained or discolored and softer than the relatively hard healthy tooth. Hand instruments are sometimes used to aid in detection and removal of caries. Additionally, the caries may also be "blasted" out with a air abrasion unit or "vaporized" with a dental laser.

The problems posed by the formation of cavities in teeth have motivated various restorative measures and technologies in the field of dentistry. One example of such restorative measures is silver fillings, which are sometimes also referred to as amalgams. Upon detection of a cavity appearing on a tooth, a dental professional, usually a dentist, may propose the application of a silver filling. As its name implies, the silver filling is a silver-based material used to fill or close a cavity or hole in an affected tooth. The composition of such silver-based materials is well-known.

Before placement of the silver-based material in the tooth affected by the cavity, the material is in a relatively malleable, putty-like form. The material is then placed in the cavity. The material hardens in the cavity to form a snug fit with the tooth itself. Usually, no adhesive materials are used or needed to further affix the silver filling in the cavity. The restoration serves to fill the defect created in the tooth resulting from the removal of the caries and also prevents further invasion of the caries by bacteria, food impaction, or the like.

In recent years, however, the use of silver fillings in addressing the problems associated with cavities has not been exclusive. Various factors and considerations have prompted the proposal and use of new restorative dental techniques that do not employ the use of silver-based materials as fillings. For example, growing aesthetic sensibilities have likely emphasized some of the limitations of silver fillings. As a result of their composition, silver fillings appear very conspicuously in the teeth of the persons having the restorations. As is well known, silver fillings appear in a person's mouth as dark but lustrous in stark contrast to the otherwise ivory-like background of natural tooth enamel.

As another example, some countries apparently have altogether abandoned the use of silver fillings for cavities. Such abandonment has been, at least in part, due to concern about their safety. Silver fillings typically will contain some amounts of mercury. The presence of mercury in silver fillings is, according to some, the cause of many health-related problems and afflictions for persons having such silver filings. Arguably, no definitive scientific data apparently establishes or dismisses any link between the use of silver fillings and the onset of medical or health problems. Nonetheless, justifiably or not, widespread health concerns have been another factor in the more limited use of silver fillings. The introduction and development of composites, or resins, including composite fillings, as restorative materials, have also led to the diminished use of silver fillings. Composite, resin, or white fillings have been around for about two decades. Composite fillings are typically composed of an organic polymer known as bisphenol-A-glycidyl methacrylate (BIS-GMA), and inorganic particles such as quartz, borosilicate glass, and lithium aluminum silicate.

As popular and effective as composite fillings are compared to silver fillings, both are similar in their susceptibility to possible damage. Both silver fillings and composite fillings alike may require repair, replacement, or restoration after long or excessive wear, failure due to leakage at the margins, recurrent caries, or undue impact. As a result of excessive wear, silver fillings may lose structural strength. Portions of a silver filling, or the entire filling itself, may weaken, loosen, or simply break off after such wear. To remedy such an event, when only a portion of the silver filling has fallen off, the silver filling may be repaired by replacing the portion of the silver filling broken off with a new silver piece. Alternatively, the entire silver filling, even the portion still attached to the tooth, may be intentionally removed by a dental professional and replaced with a new entire silver filling. Similarly, if the silver filling has fallen off entirely from a tooth, a new silver filling may be prepared to simply substitute for the missing silver filling in the tooth.

Composite fillings may also require repair. Typically, when composite fillings have been damaged by excessive wear or impact, the entire composite filling is replaced, even when only a portion of the composite fillings is damaged or broken off. This is true because the bond strength of composite materials is maximized when the composite is bonded to a tooth surface, rather than to the surface of other composite material.

The repair of composite fillings highlights both advantages and disadvantages in the use of composite materials as restorative materials in dentistry. Composite fillings have without question gained popularity, at least in part, due to their aesthetic qualities. Composite fillings, which are designed in varying shades to match the shade of the teeth into which they are placed, reside relatively inconspicuously in teeth. Because they are designed and selected to seamlessly blend into their visual environment, the composite fillings, and their boundaries often cannot be identified by the naked eye of a dental professional. As a result, when circumstances warrant the removal of a composite filling from a tooth, usually as a repair or replacement measure thereto, it can be extremely difficult for a dental professional to do so. First, the composite filling may be difficult to identify or distinguish from the tooth itself. Second, even if it can be generally located, the precise boundary of the composite filling may be difficult to discern from the surface of the tooth. Because of these and other difficulties, undue amounts of time and effort are expended by dental professionals in identifying the precise extent and dimension of the composite filling.

Various problems arise if such burdensome expenditure of time and effort associated with the prior art is not spent. If the composite filling is extracted in haste, in some circumstances, some remnants of the original composite filling may be left within the tooth. The new composite fillings will then be placed in the tooth alongside these remnants, causing poor bonding of the new composite filling with the tooth. The poor bonding may, in turn, invite further future damage or accelerated weary and early failure to the filling and possibly the tooth as well. Additionally, the poor bonding of the composite filling may lead to increased sensitivity of the nerves, staining of the margins, fracturing of the tooth, or the like. In other circumstances, a hasty attempt to remove a damaged composite filling may result in some portion of the healthy tooth being also removed, weakening of the remaining tooth, damage to the pulp, sensitivity, or the like.

The costs of spending substantial time and effort in attempts to identify the composite filling for restorative purposes burden both the dental professional as well as the patient. Filling damage is a widespread phenomenon. As a result, filling repair or replacement may constitute a significant portion of a dental professional's entire practice. The dental professional is therefore burdened by a procedure that impinges on the dental professional's ability to attend to other, and perhaps more, serious dental problems or conditions. Also, the patient may be charged an amount commensurate with the dental professional's efforts in treating composite filling damage. Such charges are inextricably, either directly or indirectly, tied to the time and effort devoted by the dental professional in performing such services. Clearly, the inability to efficiently and precisely locate the composite filling poses distinct drawbacks to both the dental professional and patient at least.

SUMMARY OF THE INVENTION

The present invention solves the problems associated with the prior art by providing methods and systems for selectively staining dental composite materials in restorative applications.

In accordance with one aspect of the present invention, a disclosing agent is provided to an applicator. The disclosing agent in the applicator is delivered to a surface of a tooth having a composite material. A stain is selectively caused after the disclosing agent is delivered to the tooth surface to allow visual distinction between the tooth and the composite material.

In accordance with another aspect of the present invention, the composite material is removed.

In accordance with yet another aspect of the present invention, the delivering of the disclosing agent, the selective causing of the stain, and the removing of the composite material is repeated until a desired amount of the composite material is entirely removed.

In accordance with yet still other aspects of the present invention, the color of the tooth is unchanged while the composite material is stained.

In accordance with yet still further aspects of the present invention, the tooth is stained while the color of the composite material is unchanged.

In another aspect, the present invention provides a kit for identifying a composite filling in a tooth. The kit comprises a disclosing agent and instructions for use. The instructions for use can include any of the methods described herein. Optionally, the kit can further include a container and an applicator, such as a syringe, brush, pellet, sprayer, swab, sponge, or the like. The instructions for use can be printed directly on the container or on a separate medium.

These and other embodiments of the present invention, as well as their advantages and features, are described in more detail in conjunction with the text below and attached figures.

DESCRIPTION OF THE SPECIFIC EMBODIMENTS

The methods and systems for selectively staining dental composite materials in accordance with the present invention are now described. The present invention relates to a new, innovative technique to greatly improve and advance restorative techniques for the treatment of, for example, tooth decay and resulting cavities in teeth. As one example, the methods and systems of the present invention overcome disadvantages associated with the repair or replacement of composite fillings in the prior art. As another example, the present invention allows for the identification of the precise location of a composite material in a tooth to facilitate repair or replacement of the composite material.

Figure 1A:
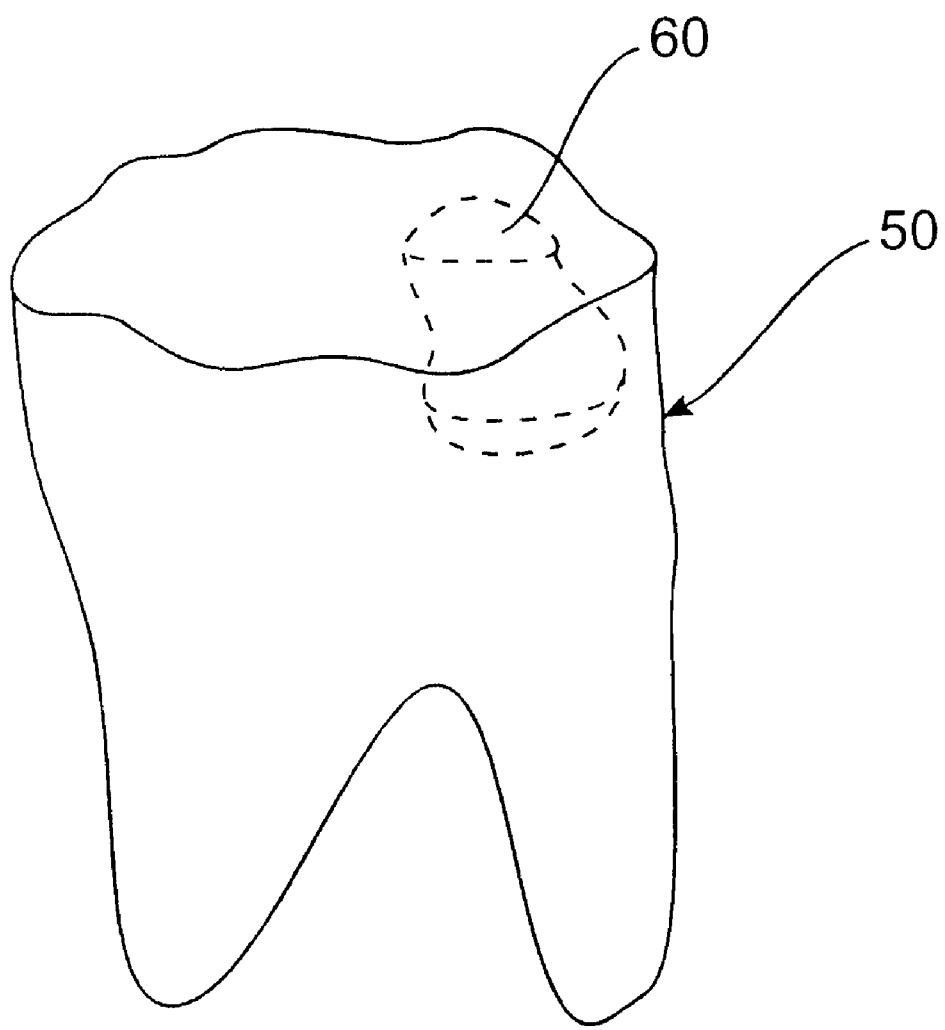
FIG. 1A illustrates a tooth and a composite filling in accordance with one of many embodiments of the present invention.

FIG. 1A illustrates a tooth 50 having a composite material 60. In one embodiment of the present invention, the tooth 50 can be any tooth of a person. In another embodiment of the present invention, the tooth 50 could be the tooth of a non-human entity. In one embodiment of the present invention, the composite material 60 has a restorative purpose. In accordance with the methods and systems of the present invention, restoration can generally be defined as any material or item placed on or in a tooth to, in whole or in part, restore the original appearance, health, or integrity of the tooth. Restorative materials can be used in a variety of contexts, including, for example, applications requiring crowns and fillings. Generally, tooth-colored restorative materials can be classified as three kinds of materials: (1) composite resins, (2) porcelains or ceramics, and (3) combination of composite resins and porcelains or ceramics. Of course, the present invention can include other applications for composite materials in dental-related applications apart from restorative applications.

The use of composite materials in restorative techniques has prompted composite fillings to be proposed as alternates for silver fillings. When composite fillings were first used in the treatment for cavities, they presented an alternative to the relatively unsightly appearance of silver fillings. However, composite fillings suffered from various drawbacks. These drawbacks were especially pronounced in treating cavities in back teeth, which are subject to more intense chewing use and force. For example, composite fillings did not bond well to teeth and occasionally failed due to loss of bond to the surrounding tooth structure. As another example, the material strength of composite fillings, i.e., their structural integrity, is often inadequate which may lead to accelerated wear and an early failure. As a result, composite fillings did not initially gain widespread acceptance in the dental community.

The development and improvement of technology relating to composite fillings, however, has now improved their physical properties, and has increased their popularity and use. Today, the materials constituting composite fillings have rendered composite fillings stronger and more durable. The wear resistance of composite fillings is now approaching or equal to that of silver filings. Furthermore, empirical evidence now suggests that composite fillings bonded in teeth actually strengthen the tooth more than silver fillings do. In view of the increasing merits of composite fillings, the dental industry has seen and continues to see a distinct trend favoring composite fillings over silver fillings. Composite fillings have also been used as indirect fillings, i.e., when the filling is first formed outside the tooth and later cemented in the tooth.

The increasingly popular use of composite fillings has in turn caused increasing frequency in the repair, replacement, and restoration of composite fillings and other composite materials used in dental applications. The difficulty in repairing and restoring composite materials is based in part on the very attributes that contribute to their popularity. Composite fillings reside relatively inconspicuously in teeth to match the shade of the tooth into which they are placed. Thus, their precise location often cannot easily be identified by the naked eye of a dental professional. The removal of an existing composite resin restoration is similar to the procedure for removal of caries. The first step typically involves identification of the composite in the tooth. The main difference is that distinguishing between the composite filling material and the surrounding tooth can be much more difficult due to the often near identical visual and surface hardness characteristics of the composite and tooth. Therefore the two qualities that dentists have often relied upon in the identification of tooth caries, visual appearance and surface hardness, are often unavailable in the identification of composite in a tooth. Difficulty in the identification of composite fillings significantly complicates repair, replacement, restoration, removal, or other manipulation of composite fillings, or other composite materials.

Like dental caries, composite material can be removed from a tooth through the use of a dental handpiece, air abrasion, or a dental laser. However, in the case of a composite restoration which closely matches the tooth in color and shade, the dentist is often left guessing as to the true location of the filling within the tooth. Removal of the composite can become a time-consuming process as the dentist must proceed slowly and cautiously in an attempt to minimize damage to the surrounding healthy tooth. Often times, some of the surrounding healthy tooth is inadvertently removed along with the composite. The methods and systems of the present invention provide innovative techniques to help overcome such complications associated with the prior art.

Figure 1B:
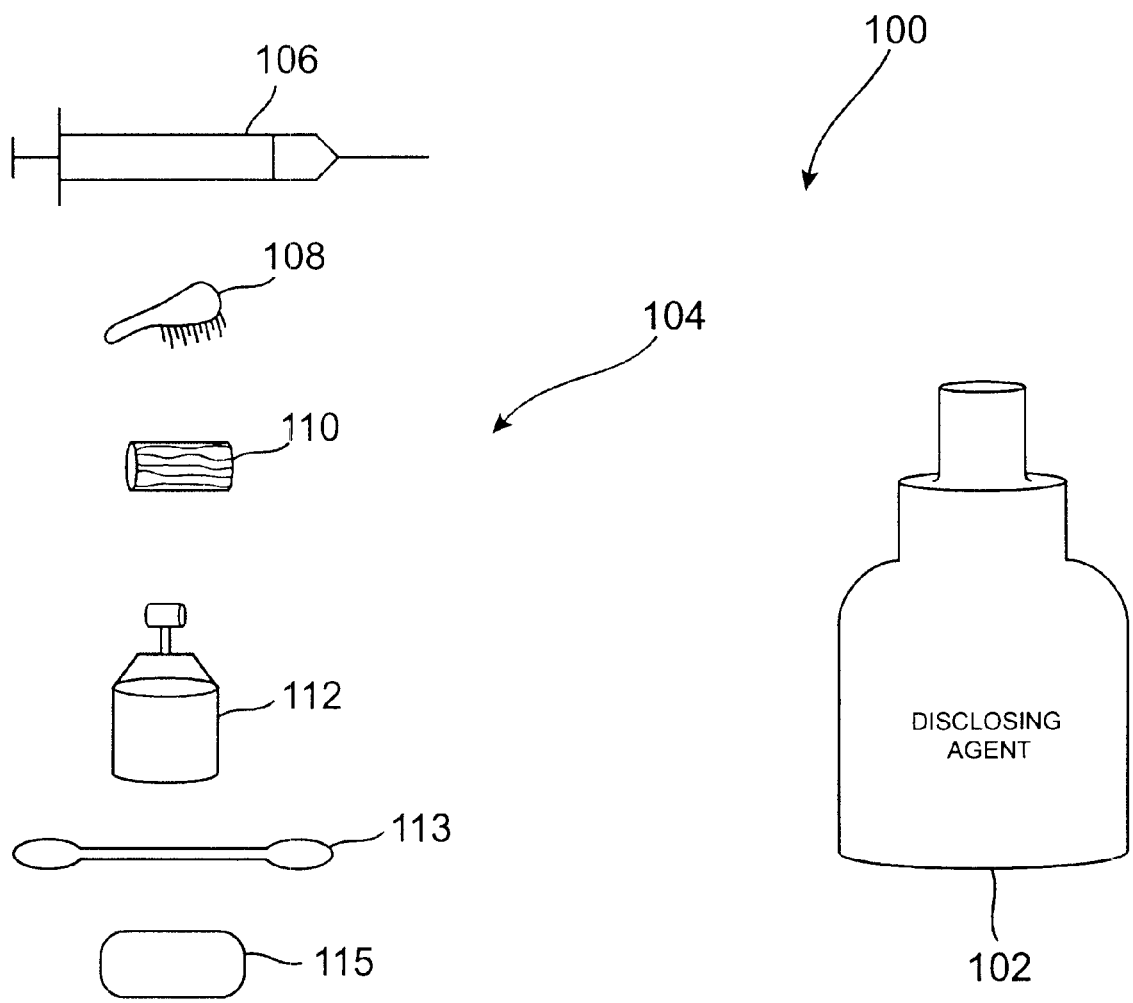
FIG. 1B illustrates a system including a disclosing agent and applicators in accordance with one of many embodiments of the present invention.

FIG. 1B illustrates a system 100 in accordance with the present invention. The system 100 includes a disclosing agent 102 and an applicator 104. The disclosing agent 102 and the applicator 104 are employed to precisely determine the extent, dimension, and location of a composite filling in a tooth. In one embodiment of the present invention, the composite filling is identified to facilitate the removal or repair of the composite filling.

The disclosing agent 102 is provided to the applicator 104 in a conventional manner for delivery of the disclosing agent 102 to the tooth and composite filling. The applicator 104 is then used to deliver the disclosing agent 102 to the affected tooth and composite filling in a conventional manner. In one embodiment of the present invention, the disclosing agent 102 is any inorganic liquid material that, in recognition of the filling as a composite material, would stain the filling. In another embodiment, the disclosing agent 102 could be organic. In addition to being liquid, the disclosing agent 102 could also be in a solid, gel-form, or gaseous form. The applicator 104 could be a syringe 106, a brush 108, a cotton pellet 110, a sprayer 112, a swab 113, a sponge, 115 for delivering the disclosing agent 102 to an intended area. Other applicators capable of applying or dispensing the disclosing agent 102 on a tooth having a composite filling are possible as well, depending in part on the form of the disclosing agent 102.

Figure 2:
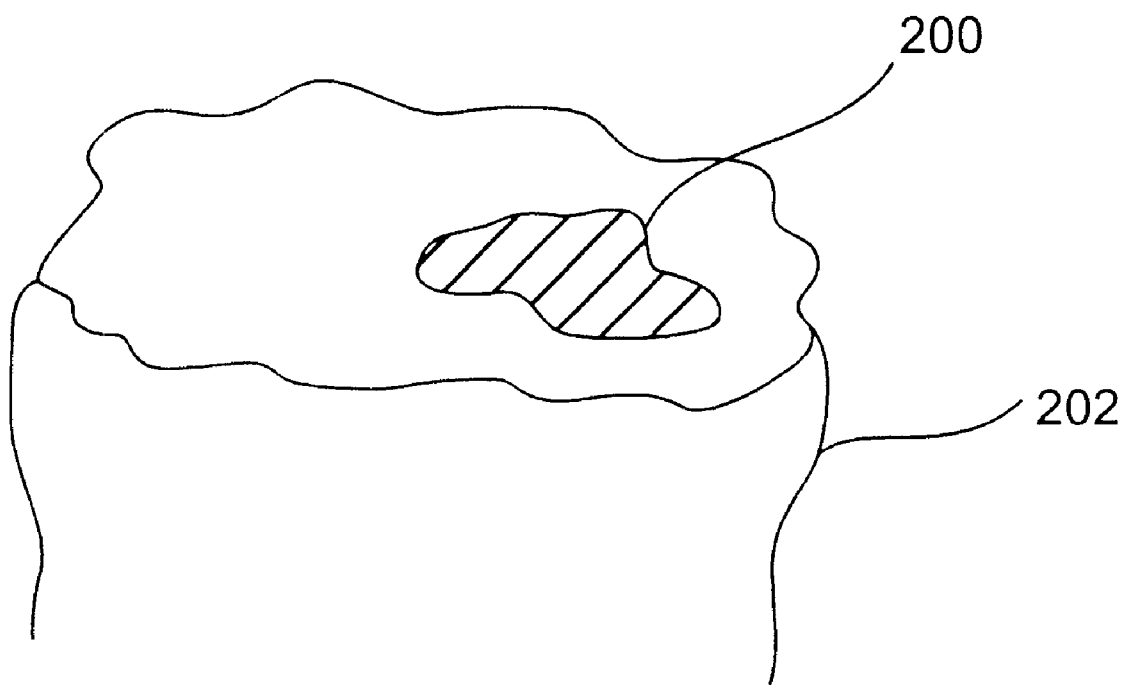
FIG. 2 illustrates a portion of a tooth and a stained composite filling in accordance with one of many embodiments of the present invention.

Upon contact with the tooth and composite filling, after a duration or immediately, the disclosing agent 102, as its name implies, discloses the existence of the composite filling. The disclosure could occur in different ways. In one embodiment of the present invention, the disclosing agent 102 reacts chemically with the surface of the composite filling to which it is exposed. The reaction forms a bond between the disclosing agent 102 and the composite filling. FIG. 2 illustrates a composite filling 200 in a tooth 202. The disclosing agent is delivered to the composite filling 200, causing a bond therebetween. In one embodiment of the present invention, the nature of the bond causes a color or shade change in the exposed areas of the composite filling 200 only and not the tooth 202 itself. The new color or shade of the composite filling 200 serves as a visual distinction between the composite filling 200 and the tooth 202. The visual distinction created in this way after application of the disclosing agent 102 allows a dental professional to easily discern the presence and boundary of the composite filling 200. Such discernment greatly facilitates and simplifies restorative techniques, particularly identification and removal, repair, or replacement of a damaged composite filling.

Figure 3:
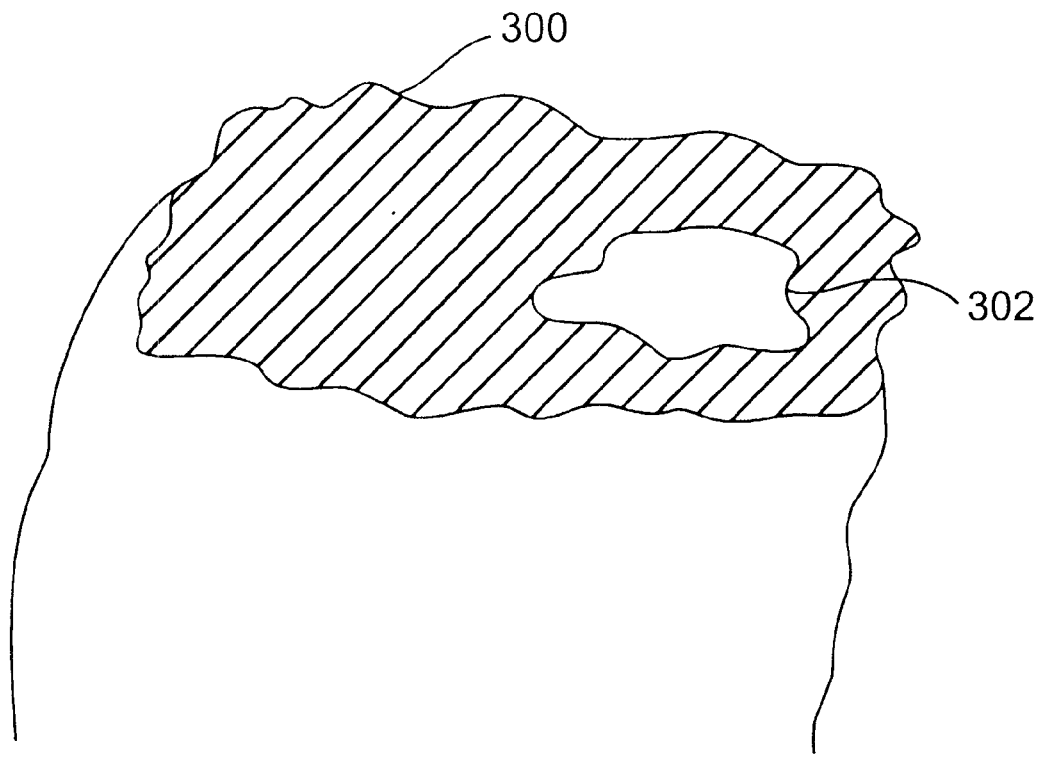
FIG. 3 illustrates a portion of a stained tooth and a composite filling in accordance with one of many embodiments of the present invention.

In another embodiment of the present invention, the disclosing agent 102 bonds with the tooth surface rather than the composite filling. FIG. 3 illustrates a tooth 300 having a composite filling 302. The disclosing agent 102 is applied by the applicator 104 to an area of the tooth 300 containing the composite filling 302. The disclosing agent 102 bonds with the surface area of the tooth exposed to the disclosing agent 102. The nature of the bond causes a color or shade change in the areas of the tooth 300 exposed to the disclosing agent 102. The new color or shade of the tooth 300 serves as a stain to provide a visual distinction between the composite filling 302 and the tooth 300. The visual distinction allows for easy and precise detection of the composite filling 302 in the tooth 300 for ultimate replacement or repair of the composite filling 302. In one embodiment of the present invention, the color or shade change in the tooth 300 is temporary only.

Figure 4:
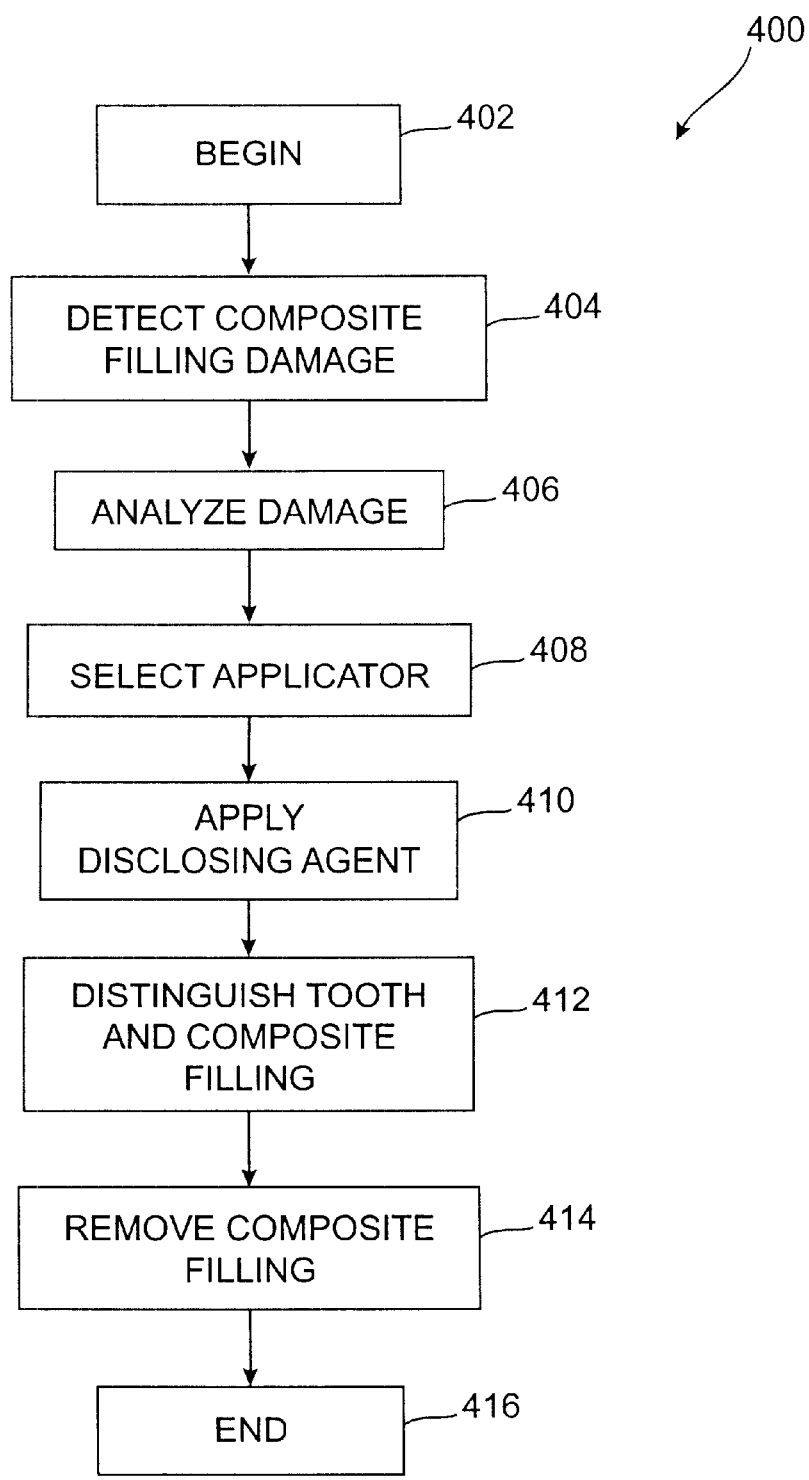
FIG. 4 illustrates a flow diagram for composite filling restoration in accordance with one of many embodiments of the present invention.

FIG. 4 is a flow diagram 400 of a process in accordance with one of many possible embodiments of the present invention. The flow diagram 400 relates to an identification of the location and extent of a composite filling upon discovery of damage to the composite filling. At a step 402, the flow diagram 400 begins and proceeds to a step 404. At the step 404, damage to a composite filling is detected by, for example, a dental professional. The detection may occur, for example, during a routine dental examination. As another example, detection of damage to a composite filling may occur after onset of patient discomfort in the affected tooth area and resulting investigation by a dental professional. The investigation can be performed by the naked human eye or with the aid of dental x-rays or other imaging techniques.

The flow diagram 400 proceeds to a step 406 where the damage to the composite filling is analyzed. Based on the analysis of the extent of damage to the composite filling, a decision is made to replace or repair the composite filling. In most cases of damage to a composite filling, the composite filling will be replaced in its entirety with a new composite filling. Complete replacement is desirable for many reasons. One reason, as an example, is to maximize the bond between the composite filling and the tooth itself to better preserve the dental restoration and increase the potential serviceable life of the filling. Another reason, as another example, is to maximize the strength and integrity of the tooth.

The flow diagram 400 proceeds to a step 408, where an applicator is selected. The dental professional selects a desired applicator to be employed in the provision of a disclosing agent on the affected tooth areas. A syringe, a brush, a cotton pellet, a sprayer, or other suitable device may be used to apply the disclosing agent on the composite filling. The selection may depend on many factors, such as ready availability, relative expense, and suitability based on the patient's needs or location of or access to the composite filling requiring attention.

The flow diagram 400 proceeds to a step 410 where the disclosing agent is delivered or otherwise applied on or in vicinity of the composite filling by the selected applicator. The disclosing agent is applied to the composite filling using a technique appropriate to the utility of the applicator. For example, if a brush is used, the brush is first exposed to the disclosing agent and then applied to the area of the composite filling. Likewise, if the applicator is a cotton pellet, the cotton pellet is first dipped in the disclosing agent and then applied to the composite filling in a dabbing manner. As another example, if the applicator is a syringe, the disclosing agent is first contained in the syringe and then expelled onto the affected composite filling area. As yet another example, if the applicator is a spray, the disclosing agent is sprayed onto the affected composite filling area.

Once the disclosing agent is applied to the composite filling, the flow diagram 400 proceeds to a step 412 where the disclosing agent stains the composite filling, causing an identification of the composite filling within the tooth. The stain allows for distinction between the composite filling and surrounding tooth. The flow diagram 400 proceeds to a step 414 where the composite filling identified using the disclosing agent is removed or repaired, as circumstances warrant. The flow diagram 400 proceeds to a block 416 where the flow diagram 400 ends.

Figure 5:
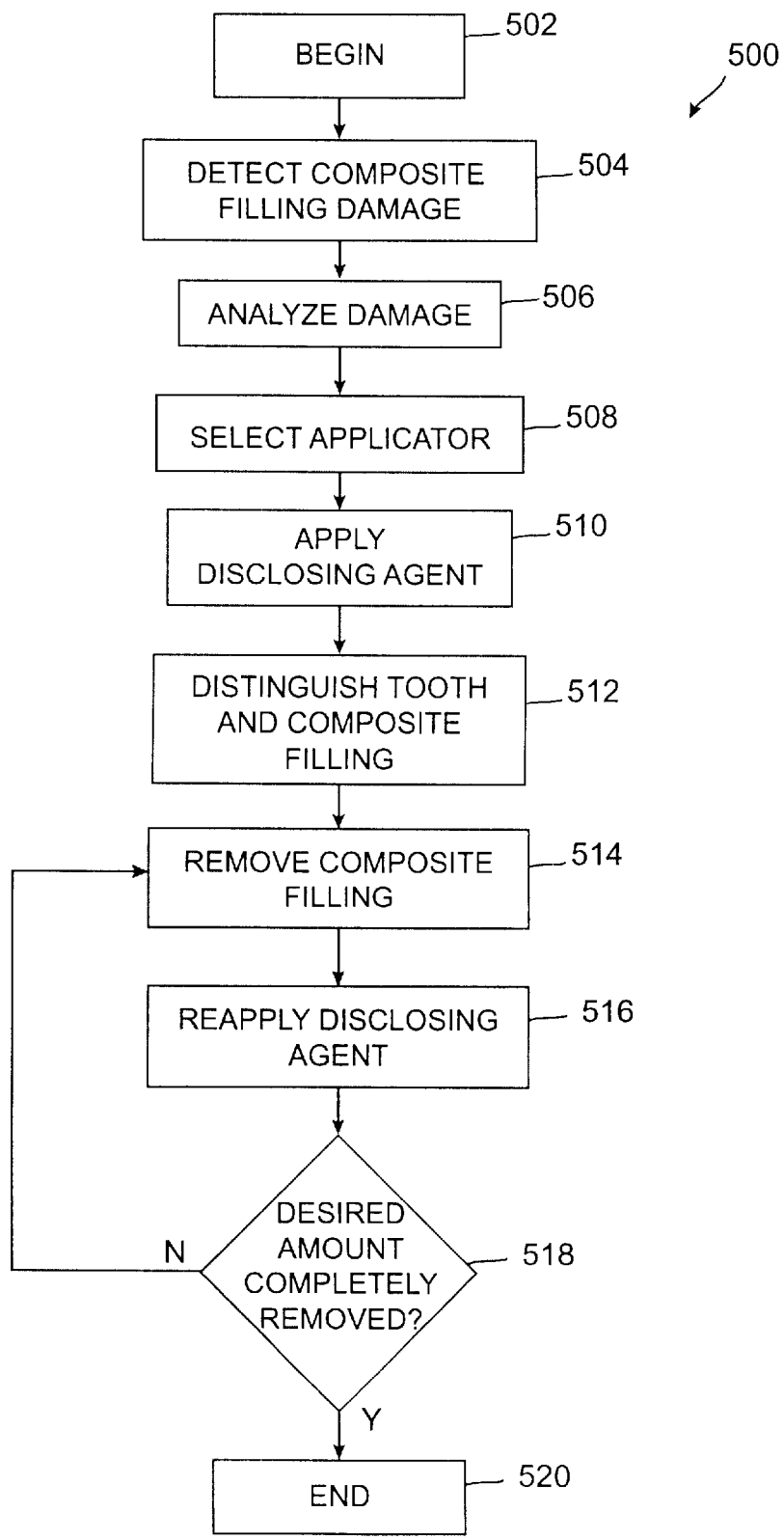
FIG. 5 illustrates a flow diagram for selective application of a disclosing agent in composite filling restoration in accordance with one of many embodiments of the present invention.

FIG. 5 is a flow diagram 500 of a process in accordance with one of many possible embodiments of the present invention. The flow diagram 500 relates to an identification of the location and extent of a composite filling upon discovery of damage to the composite filling. The flow diagram 500 also allows for selective reapplication of the disclosing agent during repair or restoration of the composite filling. Steps 502 through 514 of the flow diagram 500 are identical to the associated steps 402 through 414 of the flow diagram 400.

At a step 502, the flow diagram 500 begins and proceeds to a step 504. At the step 504, damage to a composite filling is detected by, for example, a dental professional. The detection may occur, for example, during a routine dental examination. As another example, detection of damage to a composite filling may occur after onset of patient discomfort in the affected tooth area and resulting investigation by a dental professional. The investigation can be performed by the naked human eye or with the aid of dental x-rays or other imaging techniques.

The flow diagram 500 proceeds to a step 506 where the damage to the composite filling is analyzed. Based on the analysis of the damaged composite filling, a decision is made to replace or repair the composite filling. In most cases of damage to a composite filling, the composite filling will be replaced in its entirety with a new composite filling. Complete replacement is desirable for many reasons. One reason, as an example, is to maximize the bond strength between the composite filling and the tooth itself to better preserve the dental restoration and increase the potential serviceable life of the composite filling. Another reason, as another example, is to maximize the strength and integrity of the tooth.

The flow diagram 500 proceeds to a step 508, where an applicator is selected. The dental professional selects a desired applicator to be employed in the provision of a disclosing agent on the affected tooth areas. A syringe, a brush, a cotton pellet, a sprayer, or other suitable device may be used to apply the disclosing agent on the composite filling. The selection may depend on many factors, such as ready availability, relative expense, and suitability based on the patient's needs or location of or access to the composite filling requiring attention.

The flow diagram 500 proceeds to a step 510 where the disclosing agent is delivered or otherwise applied on or in vicinity of the composite filling by the selected applicator. The disclosing agent is applied to the composite filling using a technique appropriate to the utility of the applicator. For example, if a brush is used, the brush is first exposed to the disclosing agent and then applied to the area of the composite filling. Likewise, if the applicator is a cotton pellet, the cotton pellet is first dipped in the disclosing agent and then applied to the composite filling in a dabbing manner. As another example, if the applicator is a syringe, the disclosing agent is first contained in the syringe and then expelled onto the affected composite filling area. As yet another example, if the applicator is a spray, the disclosing agent is sprayed onto the affected composite filling area.

Once the disclosing agent is applied to the composite filling, the flow diagram 500 proceeds to a step 512 where the disclosing agent stains the composite filling, causing an identification of the composite filling within the tooth. The stain allows for distinction between the composite filling and surrounding tooth. The flow diagram 500 proceeds to a step 514 where the composite filling identified using the disclosing agent is removed or repaired, as circumstances warrant.

The flow diagram 500 proceeds to step 516 where a disclosing agent is reapplied to the tooth. The flow diagram then proceeds to decision block 518 where a determination is made on whether the desired amount of the composite filling to be removed or repaired has been entirely removed. For example, in the instances where the composite filling has been completely removed, there will be no staining of the composite. In other instances, if the dentist only removed a portion of the composite filling, the composite filling would be stained.

If the result at step 518 is affirmative (e.g., the desired amount of composite is removed), the flow diagram 500 proceeds to a block 520 where the flow diagram 500 ends. If the result of the decision block 518 is negative (e.g., the desired amount of composite has not been removed), the flow diagram proceeds back to step 514 where more repair or restorative effort is performed. In such an instance, a better distinction between the tooth and the composite filling is needed for the repair or restoration of the composite filling. Such a need could arise, for example, in the piecemeal extraction of a composite filling. In this regard, if a portion of the composite filling is removed, the underlying layer or remaining portions, which were not initially exposed to the disclosing agent, would require further staining to allow identification of the boundaries of remaining portions of the composite filling.

Figure 6:
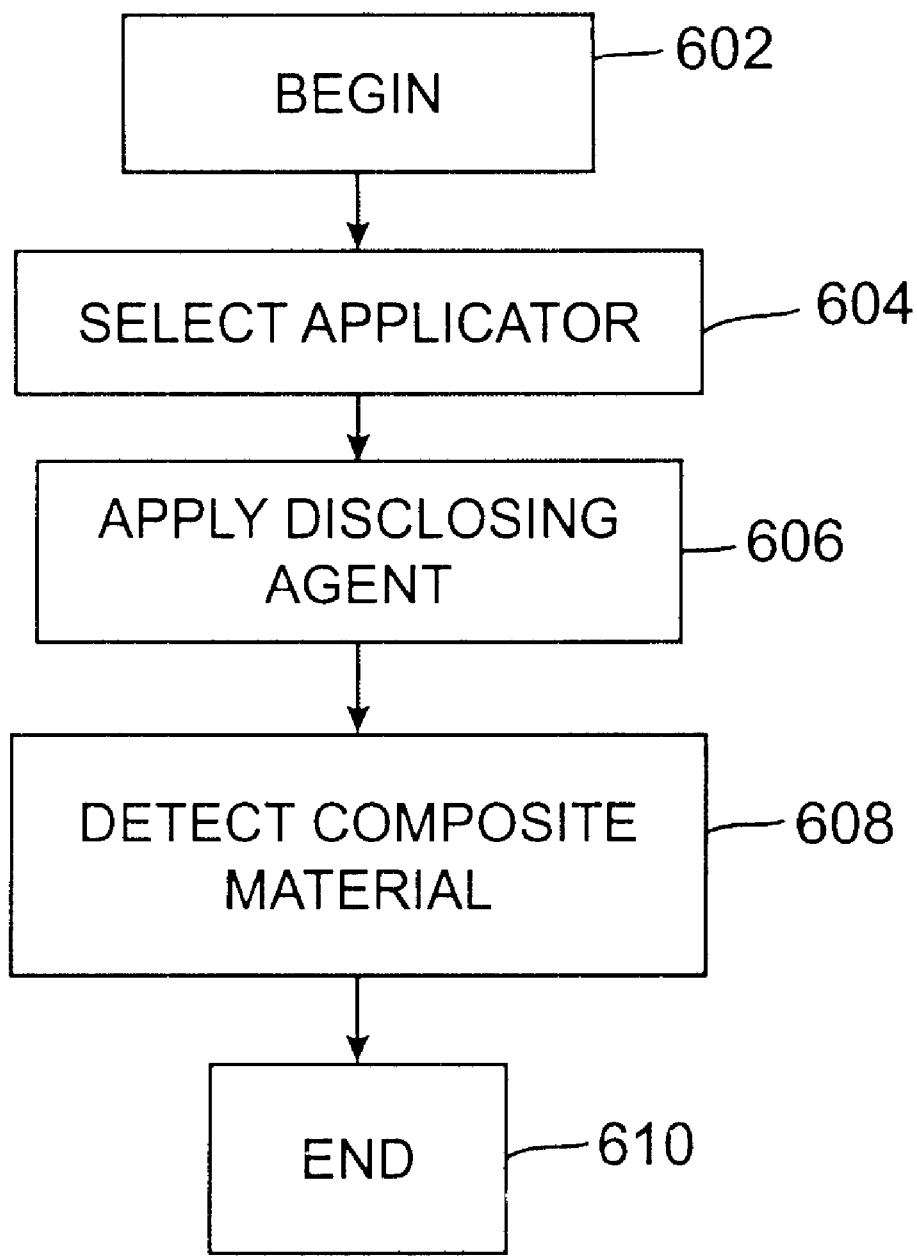
FIG. 6 illustrates a flow diagram for composite material detection in accordance with one of many embodiments of the present invention.

FIG. 6 is a flow diagram 600 of a process in accordance with another of many possible embodiments of the present invention. The flow diagram 600 relates to detection of composite materials in teeth and assessment of their condition or examination for possible damage thereto. The flow diagram 600 begins at a step 602 and proceeds to a step 604. At the step 604 an applicator is chosen by a dental professional. The applicator is chosen based on a variety of factors, as discussed above. The flow diagram 600 proceeds to a step 606 where the disclosing agent is applied by the applicator to all or a select number of teeth. The flow diagram proceeds to a step 608 where, after application to the teeth, the disclosing agent selectively stains or otherwise visually identifies the composite fillings of the teeth. Alternatively, as stated above, the disclosing agent may selectively stain or otherwise visually identify the teeth, as opposed to the composite fillings. Such visual distinction allows for the detection of composite materials in teeth for any number of possible purposes. The logic proceeds to a step 610 where the flow diagram 600 ends.

The disclosing agent may take a variety of forms and may be crosslinked with the composite material in a variety of methods. For example, one method would be to chemically attach a dye molecule to the crosslinked methacrylate surface. Another method would be to chemisorb or physisorb the dye molecule to the crosslinked methacrylate surface.

One reaction scheme that could be used to chemically bond the dye molecule to the polymer surface would be to first halogenate the surface. Then, using a suitably modified dye molecule, replace the halogen entity with the dye. Examples of this type of reaction are outlined as follows:

(1A) Replace a Hydrogen (Anywhere in the Polymer) with a Halogen Atom (Cl or Br)

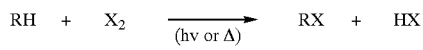

R is any hydrocarbon (i.e., all of the polymer except the H to be removed),

X is Cl or Br, hv is UV light, and

Δ is heat.

This reaction may be done in the liquid phase with a peroxide initiator instead of the UV light or heat. The reaction is very exothermic when X—Cl and slightly exothermic when X=Br. Also, Br is less reactive than Cl.

Then ps (2A) React a Hydroxyl-functionalized Dye Molecule with the Halogenated Polymer

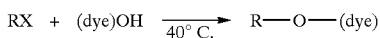

R is the polymer (dye)OH is any colored dye that has been functionalized with an hydroxyl group (with or without a hydrocarbon spacer in between), and (dye) is the dye core which has been attached to the polymer via reaction with hydroxyl groups (producing an ether linkage between the dye and the polymer).

Or (1B) Replace a Hydrogen on an Aryl Ring in the Backbone of the Polymer

Ar is the aryl (hydrocarbon ring) group in the backbone of the polymer, and

Tl(OOCCF$_3$)$_2$ is thallium trifluoroacetate dissolved in CF$_3$COOH (trifluoroacetic acid).

Then (2B) React a Hydroxyl-functionalized Dye Molecule with the Polymer

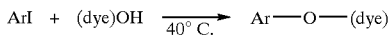

Ar is the polymer, and (dye)OH is the OH-functionalized dye.

This is one type of reaction scheme that can be used to functionalized the crosslinked polymer with dye molecules. It should be appreciated however, that this is not the only type of chemical reaction that can accomplish this goal, and the present invention is not limited to these specific chemical reactions.

Types of dyes could include, but not be limited to, stilbenes, anthraquinones, diazo dyes, triarylmethanes, monoazo dyes, rhodamines, and the like.

Another method for chemically bonding a dye to the methacrylate polymer would be to first incorporate amine groups (NH$_2$) into the polymer. Because of the carbonyl groups (C=O) in the polymer, the amine would be part of an amide group (NHCO). After the amine groups have been added, it would be possible to incorporate a dye molecule by crosslinking using the amide groups. Molecular Probes, Inc. of Eugene, Oreg. produces dyes that can be crosslinked in this fashion.

One example reaction to add amine groups to the polymer group would be:

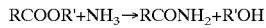

R is one part of the polymer,

COO is the ester linkage characteristic of methacrylate polymers, and

R' is the other part of the polymer.

Yet another method of bonding a dye molecule on the surface of the methacrylate polymer is to use some property of the dye which gives it an affinity to the polymer. Depending on the property used, the dye can be used to chemisorb or physisorb on the surface of the polymer. Since it is desirable to have the dye preferentially adsorb to the polymer and not to the tooth surface, a property which is different from the two surfaces is required. An example might be to use hydrophilicity/hydrophobicity. The tooth surface is very hydrophilic whereas the polymer surface is hydrophobic. By choosing a dye which is inherently hydrophobic, it will tend to aggregate on the polymer surface rather than on the tooth surface.

Dyes that are hydrophobic include, but are not limited to, acid fuchsin, xylidine ponceau, acridine orange, and the like.

Other properties which may be considered for this type of adsorption are hydrogen-bonding, chemical affinity, aromaticity, or the like.

Figure 7:
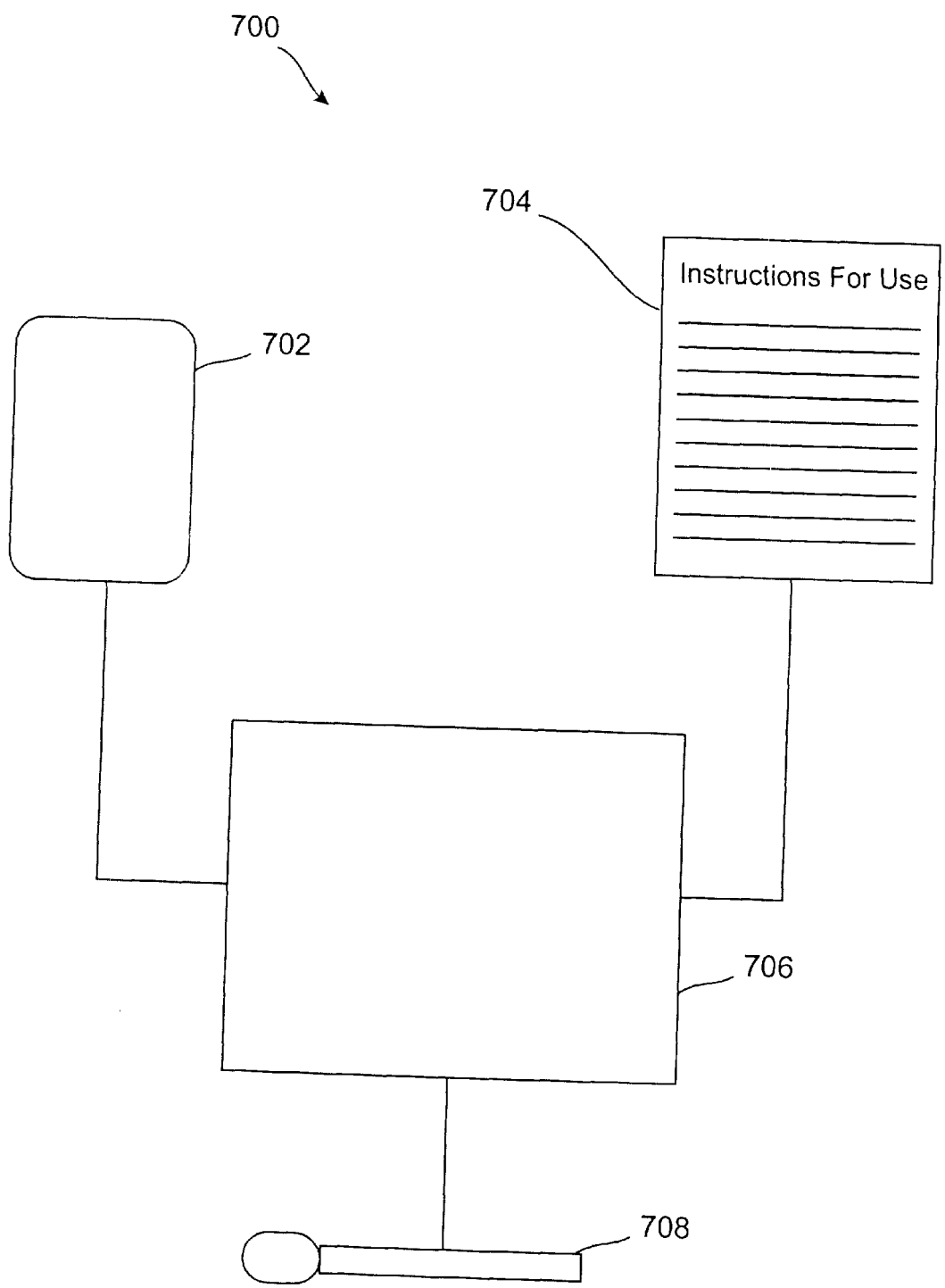
FIG. 7 illustrates a kit of the present invention.

In another aspect, the present invention provides kits 700. As illustrated in FIG. 7, kits according to the present invention can include a disclosing agent 702 in a container. The kits will further include instructions for use 704 setting forth a method as described above. Optionally, the kits will further include an applicator 706 and packaging 708 suitable for containing the disclosing, applicator, and the instructions for use. Exemplary containers include pouches, trays, boxes, tubes, and the like. The instructions for use may be provided on a separate sheet of paper or other medium. Optionally, the instructions may be printed in whole or in part on the packaging. Usually, at least the applicator will be provided in a sterilized condition.

As will be understood by those with ordinary skill in the art, the present invention may be embodied in other specific forms without departing from the spirit or essential characteristics thereof. For example, the restorative composite material 60 is depicted to be associated with one tooth 50. However, it will be readily appreciated by one of ordinary skill in the art that the composite material 60 could also be associated with more than one tooth for a particular purpose. Accordingly, the methods and systems discussed above with regard to the application of a disclosing agent to reveal the precise location and extent of the composite material would also apply to composite material contained in or otherwise associated with more than one tooth.

Additionally, while the above composites are described in relation to particular polymers, it should be appreciated that the present invention can be used with a polymer with a variety of substituents on the backbone. Also, the hydrocarbon group can include other functional groups of polymers which are well known to those of ordinary skill in the art, such as keytone, esther, amide, ether, and other hetero-atom functional groups. Moreover, the aryl group can also include one or more substituents that are well known to one of ordinary skill in the art, such as halide, alkoxide, hydroxide, amines, carbonyl groups, and the like.

Furthermore, some embodiments of the present invention have been discussed with respect to restorative techniques involving composite fillings in particular. It will be appreciated by those of ordinary skill in the art that the present invention applies equally to other restorative techniques that do not necessarily involve composite fillings. For example, the techniques of the present invention also apply to the repair and restoration of dental crowns, veneers, and other dental implements that are made of composite materials. The present invention applies to any dental procedures or applications involving precise detection of composite materials that are difficult to discern with conventional techniques.

Likewise, the present application has been exemplarily discussed in regard to applications involving repair or restoration of composite material. It will be appreciated that, in yet other embodiments of the present invention, the present invention would apply to the use of composite materials for non-restorative purposes. In this regard, techniques of the present invention would apply to composite materials used for, for example, a cosmetic purpose to alter the original or earlier appearance of the tooth.

Furthermore, it should be understood that the ability of the present invention to allow distinction between the composite material and the tooth contemplates relative shading. In accordance with one embodiment the present invention, the tooth could be stained while the appearance of the composite material is unchanged. In another embodiment, the composite material could be stained while the appearance of the tooth is unchanged. In yet another embodiment, the tooth and the composite material could both be stained in varying colors or shades as long as the staining causes a ready visual distinction between the tooth and the composite material. Accordingly, the embodiments of the present invention discussed above, as well as those illustrated, include any and all variations that allow for visual distinction of the tooth and the composite material, even if some but not all such variations were explicitly described above.

As will be understood by those with ordinary skill in the art, the present invention may be embodied in other specific forms without departing from the spirit or essential characteristics thereof. Also, implementations shown in the figures or described in text are but some of many possible embodiments which may be designed to take advantage of the method and system of the present invention. Equivalents and alternatives, and others, are intended to be included within the scope of the present invention. Accordingly, for an understanding of the scope of the invention, reference should be made to the appended claims.

What is claimed is:

1. A method for identifying a dental composite material comprising:

providing a disclosing agent to an applicator;

delivering the disclosing agent in the applicator to at least one tooth having the composite material; and staining the composite material with the disclosing agent to distinguish the composite material from the at least one tooth.

2. The method of claim 1 wherein the disclosing agent is hydrophobic.

3. The method of claim 1 further comprising removing the composite material.

4. The method of claim 3 further comprising selecting an applicator.

5. The method of claim 3 further comprising repeating said delivering, said staining, and said removing until a desired amount of the composite material is entirely removed.

6. The method of claim 5 further comprising selecting an applicator.

7. The method of claim 1 wherein said delivering includes syringing, spraying, or squirting, the disclosing agent on the at least one tooth.

8. The method of claim 1 wherein said delivering includes brushing the disclosing agent on the at least one tooth.

9. The method of claim 1 wherein said delivering includes dabbing the disclosing agent on the at least one tooth.

10. The method of claim 1 wherein staining comprises chemisorbing or physisorbing the disclosing agent to the composite material.

11. A method for identifying a composite material in dental restoration comprising:

providing a disclosing agent to an applicator;

delivering the disclosing agent in the applicator to a surface of a tooth having a composite material; and selectively causing a stain after the disclosing agent is delivered to allow visual distinction between the tooth and the composite material.

12. The method of claim 11 further comprising removing the composite material.

13. The method of claim 12 further comprising repeating said delivering, said selectively causing, and said removing until a desired amount of the composite material is entirely removed.

14. The method of claim 11 further comprising:

preserving the color of the tooth; and staining the composite material.

15. The method of claim 11 further comprising:

staining the tooth; and preserving the color of the composite material.

16. A method for identifying a dental composite material in a tooth, the method comprising applying a disclosing agent selected from a group of stilbenes, anthraquinones, diazo dyes, triarylmethanes, monoaza dyes or rhodamines, to a surface of the tooth and the dental composite so as to differentiate the dental composite from the tooth.

17. A method for identifying a hydrophobic dental composite material in a tooth, the method comprising applying a hydrophobic dye to the dental composite and a surface of the tooth to differentiate the dental composite from the tooth.

18. The method of claim 17 wherein the hydrophobic dye comprises fuchsin, xylidine ponceau, or acridine orange.

19. A method of identifying a dental composite material in a tooth, the method comprising:

applying a disclosing agent onto a surface of the tooth and the dental composite material;

crosslinking the disclosing agent only to the composite material so as to dental composite material from the tooth.

20. The method of claim 19 wherein the dental composite material comprises a crosslinked methacrylate surface, wherein crosslinking the disclosing agent comprises chemically attaching the disclosing agent to the crosslinked methacrylate surface of the dental composite material.

21. The method of claim 19 wherein the dental composite material comprises a crosslinked methacrylate surface, wherein crosslinking the disclosing agent comprises chemisorbing the disclosing agent to the crosslinked methacrylate surface of the dental composite material.

22. The method of claim 19 wherein the dental composite material comprises a crosslinked methacrylate surface, wherein crosslinking the disclosing agent comprises physisorbing the disclosing agent to the crosslinked methacrylate surface of the dental composite material.

23. The method of claim 19 comprising halogenating the surface of the tooth and the dental composite material prior to applying the disclosing agent.

24. The method of claim 23 wherein applying the disclosing agent comprises replacing a hydrogen atom on the dental composite material with halogen atom from the halogenating step to create a halogenated polymer on the dental composite.

25. The method of claim 24 wherein applying the disclosing agent comprises reacting the disclosing agent with the halogenated polymer.

* * * * *